(12) United States Patent
Santra et al.

(10) Patent No.: US 11,585,891 B2
(45) Date of Patent: Feb. 21, 2023

(54) RADAR-BASED VITAL SIGN ESTIMATION

(71) Applicant: Infineon Technologies AG, Neubiberg (DE)

(72) Inventors: Avik Santra, Munich (DE); Muhammad Arsalan, Munich (DE); Christoph Will, Munich (DE)

(73) Assignee: Infineon Technologies AG, Neubiberg (DE)

( * ) Notice: Subject to any disclaimer, the term of this patent is extended or adjusted under 35 U.S.C. 154(b) by 467 days.

(21) Appl. No.: 16/853,011

(22) Filed: Apr. 20, 2020

(65) Prior Publication Data
US 2021/0325509 A1    Oct. 21, 2021

(51) Int. Cl.
*G01S 7/35* (2006.01)
*G01S 13/88* (2006.01)
(Continued)

(52) U.S. Cl.
CPC .............. *G01S 7/358* (2021.05); *G01S 7/417* (2013.01); *G01S 13/343* (2013.01); *G01S 13/56* (2013.01); *G01S 13/88* (2013.01); *A61B 5/02444* (2013.01); *A61B 5/0816* (2013.01); *A61B 5/113* (2013.01); *G01S 7/288* (2013.01); *G01S 7/2883* (2021.05); *G01S 7/2886* (2021.05); *G01S 7/295* (2013.01)

(58) Field of Classification Search
CPC .......... G01S 7/295; G01S 7/288; G01S 7/358; G01S 13/343; G01S 13/56; G01S 13/88; G01S 7/2883; G01S 7/2886; G01S 7/417; A61B 5/02444; A61B 5/0816; A61B 5/113
See application file for complete search history.

(56) References Cited

U.S. PATENT DOCUMENTS 4,241,347 A    12/1980   Mbanese et al.
5,687,733 A    11/1997   McKown
(Continued)

FOREIGN PATENT DOCUMENTS

CN    1463161 A    12/2003
CN    1716695 A    1/2006
(Continued)

OTHER PUBLICATIONS

U.S. Appl. No. 17/834,557, filed Jun. 7, 2022.
(Continued)

*Primary Examiner* — Matthew M Barker
(74) *Attorney, Agent, or Firm* — Slater Matsil, LLP (57) ABSTRACT

In an embodiment, a method includes: receiving radar signals with a millimeter-wave radar; generating range data based on the received radar signals; detecting a target based on the range data; performing ellipse fitting on in-phase (I) and quadrature (Q) signals associated with the detected target to generate compensated I and Q signals associated with the detected target; classifying the compensated I and Q signals; when the classification of the compensated I and Q signals correspond to a first class, determining a displacement signal based on the compensated I and Q signals, and determining a vital sign based on the displacement signal; and when the classification of the compensated I and Q signals correspond to a second class, discarding the compensated I and Q signals.

17 Claims, 5 Drawing Sheets

(51) Int. Cl.
*G01S 7/41* (2006.01)
*G01S 13/34* (2006.01)
*G01S 13/56* (2006.01)
*A61B 5/113* (2006.01)
*G01S 7/288* (2006.01)
*A61B 5/024* (2006.01)
*A61B 5/08* (2006.01)
*G01S 7/295* (2006.01)

(56) References Cited

U.S. PATENT DOCUMENTS

| | | |
|---|---|---|
| 6,147,572 A | 11/2000 | Kaminski et al. |
| 6,414,631 B1 | 7/2002 | Fujimoto |
| 6,636,174 B2 | 10/2003 | Arikan et al. |
| 7,048,973 B2 | 5/2006 | Sakamoto et al. |
| 7,057,564 B2 | 6/2006 | Tsai et al. |
| 7,171,052 B2 | 1/2007 | Park |
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,477,812 B2* | 10/2016 | Lin .................. G01S 7/354 |
| 9,495,600 B2 | 11/2016 | Heu et al. |
| 9,886,095 B2 | 2/2018 | Pothier |
| 9,935,065 B1 | 4/2018 | Baheti et al. |
| 10,601,630 B1* | 3/2020 | Dickerman .......... H04L 27/3809 |
| 10,795,012 B2 | 10/2020 | Santra et al. |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0074307 A1* | 3/2008 | Boric-Lubecke .... A61B 5/0507 342/28 |
| 2008/0077015 A1 | 3/2008 | Boric-Lubecke et al. |
| 2008/0106460 A1 | 5/2008 | Kurtz et al. |
| 2008/0119716 A1* | 5/2008 | Boric-Lubecke .... A61B 5/7225 600/407 |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0152600 A1* | 6/2010 | Droitcour .......... A61B 5/1113 600/534 |
| 2010/0207805 A1 | 8/2010 | Haworth |
| 2011/0299433 A1 | 12/2011 | Darabi et al. |
| 2012/0022348 A1* | 1/2012 | Droitcour .......... G01S 13/825 600/407 |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0146796 A1 | 6/2012 | Margon et al. |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2013/0176161 A1 | 7/2013 | Derham et al. |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0301167 A1 | 10/2015 | Sentelle et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0055912 A1 | 3/2017 | Gamble et al. |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0215734 A1 | 8/2017 | Yamaji |
| 2017/0364160 A1 | 12/2017 | Malysa et al. |
| 2018/0046255 A1 | 2/2018 | Rothera et al. |
| 2018/0055451 A1* | 3/2018 | Kuroyanagi .......... G01S 13/88 |
| 2018/0071473 A1 | 3/2018 | Trotta et al. |
| 2018/0101239 A1 | 4/2018 | Yin et al. |
| 2018/0279884 A1 | 10/2018 | Ahmad et al. |
| 2019/0302252 A1 | 10/2019 | Santra et al. |
| 2020/0113445 A1* | 4/2020 | Gigie .................. A61B 5/7214 |
| 2020/0367764 A1 | 11/2020 | Le Guillou et al. |

(56) References Cited

U.S. PATENT DOCUMENTS

| | | |
|---|---|---|
| 2021/0255280 A1 | 8/2021 | Santra et al. |
| 2021/0325509 A1 | 10/2021 | Santra et al. |

FOREIGN PATENT DOCUMENTS

| | | | | |
|---|---|---|---|---|
| CN | 101490578 A | | 7/2009 | |
| CN | 101585361 A | | 11/2009 | |
| CN | 102788969 A | | 11/2012 | |
| CN | 102967854 A | | 3/2013 | |
| CN | 103529444 A | | 1/2014 | |
| CN | 203950036 U | | 11/2014 | |
| CN | 106644030 A | * | 5/2017 | ............... G01H 9/00 |
| CN | 110065499 A | | 7/2019 | |
| DE | 102008054570 A1 | | 6/2010 | |
| DE | 102011100907 A1 | | 1/2012 | |
| DE | 102011075725 A1 | | 11/2012 | |
| DE | 102014118063 A1 | | 7/2015 | |
| GB | 2247799 A | | 3/1992 | |
| JP | 2001174539 A | | 6/2001 | |
| JP | 2004198312 A | | 7/2004 | |
| JP | 2006234513 A | | 9/2006 | |
| JP | 2008029025 A | | 2/2008 | |
| JP | 2008089614 A | | 4/2008 | |
| JP | 2009069124 A | | 4/2009 | |
| JP | 2011529181 A | | 12/2011 | |
| JP | 2012112861 A | | 6/2012 | |
| JP | 2013521508 A | | 6/2013 | |
| JP | 2014055957 A | | 3/2014 | |
| KR | 20090063166 A | | 6/2009 | |
| KR | 20140082815 A | | 7/2014 | |
| WO | 2007060069 A1 | | 5/2007 | |
| WO | 2013009473 A2 | | 1/2013 | |
| WO | 2016033361 A1 | | 3/2016 | |

OTHER PUBLICATIONS

U.S. Appl. No. 16/794,904, filed Feb. 19, 2020.
Wikipedia, "Kalman filter," https://en.wikipedia.org/wiki/Kalman_filter, cited in OA dated Apr. 8, 2022, 36 pages.
Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.
Vinci, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, pp. 2093-2100.
Wang, Fu-Kang et al., "Wrist Pulse Rate Monitor Using Self-Injection-Locked Radar Technology", Biosensors, MDPI, Oct. 26, 2016, 12 pages.
Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.
Will, Christoph et al., "Advanced Template Matching Algorithm for Instantaneous Heartbeat Detection using Continuous Wave Radar Systems", ResearchGate, May 2017, 5 pages.
Will, Christoph et al., "Human Target Detection, Tracking, and Classification Using 24-GHz FMCW Radar", IEEE Sensors Journal, vol. 19, No. 17, Sep. 1, 2019, pp. 7283-7299.
Will, Christoph et al., "Local Pulse Wave Detection using Continuous Wave Radar Systems", IEEE Journal of Electromagnetics, RF and Microwaves in Medicine and Biology, Oct. 25, 2017, 9 pages.
Will, Christoph et al., "Radar-Based Heart Sound Detection", Scientific Reports, www.nature.com/scientificreports, Jul. 26, 2018, 15 pages.
Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.

Tu, Jianxuan et al., "Fast Acquisition of Heart Rate in Noncontact Vital Sign Radar Measurement Using Time-Window-Variation Technique", IEEE Transactions on Instrumentation and Measurement, vol. 65, No. 1, Jan. 2016, pp. 112-122.
"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.
Chen, Xiaolong et al., "Detection and Extraction of Marine Target with Micromotion via Short-Time Fractional Fourier Transform in Sparse Domain," IEEE International Conference on Signal Processing, Communications and Computing, CSPCC, Aug. 5-8, 2016, 5 pages.
Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.
Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, pp. 1847-1855.
Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.
Deacon, Peter et al., "Frequency Modulated Continuous Wave (FMCW) Radar," Design Team 6 Technical Lecture, Nov. 9, 2011, 27 pages.
Dham, Vivek "Programming Chirp Parameters in TI Radar Devices," Application Report SWRA553, Texas Instruments, May 2017, 15 pages.
Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.
Dooring Alert Systems, "Riders Matter," http:\\dooringalertsystems.com, printed Oct. 4, 2017, 16 pages.
Filippelli, Mario et al., "Respiratory dynamics during laughter," J Appl Physiol, (90), 1441-1446, Apr. 2001, http://ap.physiology.org/content/jap/90/4/1441.full.pdf.
Fox, Ben, "The Simple Technique That Could Save Cyclists' Lives," https://www.outsideonline.com/2115116/simple-technique-could-save-cyclists-lives, Sep. 19, 2016, 6 pages.
Gigie, Andrew et al., "Novel Approach for Vibration Detection Using Indented Radar", Progess in Electromagnetic Research C, vol. 87, pp. 147-162, Oct. 4, 2018.
Gouveia, Carolina et al., "A Review on Methods for Random Motion Detection and Compensation in Bio-Radar Systems", Sensors, MDPI, Jan. 31, 2019, 17 pages.
Gu, Changzhan et al., "Assessment of Human Respiration Patterns via Noncontact Sensing Using Doppler MultiRadar System", Sensors Mar. 2015, 15(3), 6383-6398, doi: 10.3390/s150306383, 17 pages.
Gu, Changzhan et al., "Deep Neural Network based Body Movement Cancellation for Doppler Radar Vital Sign Detection", IEEE MTT-S International Wireless Symposium (IWS) May 19-22, 2019, 3 pages.
Gu, Changzhu "Short-Range Noncontact Sensors for Healthcare and Other Emerginng Applications: A Review", Sensors, MDPI, Jul. 26, 2016, 24 pages.
Gu, Changzhan et al., "From Tumor Targeting to Speed Monitoring", IEEE Microwave Magazine, ResearchGate, Jun. 2014, 11 pages.
Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.
Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, pp. 725-735.

(56) References Cited

OTHER PUBLICATIONS

Immoreev, I. Ya. "Ultrawideband Radars: Features and Capabilities", Journal of Communications Technology and Electronics, ISSN: 1064-2269, vol. 54, No. 1, Feb. 8, 2009, pp. 1-26.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWR1xxx Power Management Optimizations—Low Cost LC Filter Solution," Application Report SWRA577, Texas Instruments, Oct. 2017, 19 pages.

Kishore, N. et al., "Millimeter Wave Antenna for Intelligent Transportation Systems Application", Journal of Microwaves, Optoelectronics and Electromagnetic Applications, vol. 17, No. 1, Mar. 2018, pp. 171-178.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Li, Changzhi et al., "A Review on Recent Advances in Doppler Radar Sensors for Noncontact Healthcare Monitoring", IEEE Transactions on Microwave Theory and Techniques, vol. 61, No. 5, May 2013, pp. 2046-2060.

Li, Changzhi et al., "A Review on Recent Progress of Portable Short-Range Noncontact Microwave Radar Systems", IEEE Transactions on Microwave Theory and Techniques, vol. 65, No. 5, May 2017, pp. 1692-1706.

Li, Changzhi et al., "Random Body Movement Cancellation in Doppler Radar Vital Sign Detection", IEEE Transactions on Microwave Theory and Techniques, vol. 56, No. 12, Dec. 2008, pp. 3143-3152.

Li, Changzhi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.

Li, Changzhi "Vital-sign monitoring on the go", Sensors news and views, www.nature.com/natureelectronics, Nature Electronics, vol. 2, Jun. 2019, 2 pages.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, pp. 2542-2549.

Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Mostov, K., et al., "Medical applications of shortwave FM radar: Remote monitoring of cardiac and respiratory motion", Am. Assoc. Phys. Med., 37(3), Mar. 2010, pp. 1332-1338.

Oguntala, G et al., "Indoor location identification technologies for real-time IoT-based applications: an inclusive survey", Elsevier Inc., http://hdl.handle.net/10454/16634, Oct. 2018, 42 pages.

Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, pp. 747-757.

Santra, Avik et al., "Short-range multi-mode continuous-wave radar for vital sign measurement and imaging", ResearchGate, Conference Paper, Apr. 2018, 6 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Singh, Aditya et al., "Data-Based Quadrature Imbalance Compensation for a CW Doppler Radar System", https://www.researchgate.net/publication/258793573, IEEE Transactions on Microwave Theory and Techniques, Apr. 2013, 7 pages.

Suleymanov, Suleyman, "Design and Implementation of an FMCW Radar Signal Processing Module for Automotive Applications," Master Thesis, University of Twente, Aug. 31, 2016, 61 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Zakrzewski, M. et al., "Quadrature Imbalance Compensation with Ellipse-Fitting Methods for Microwave Radar Physiological Sensing," IEEE Transactions on Microwave Theory and Techniques, vol. 62, No. 6, Jun. 2014, 10 pages.

* cited by examiner

RADAR-BASED VITAL SIGN ESTIMATION

TECHNICAL FIELD

The present disclosure relates generally to an electronic system and method, and, in particular embodiments, to a radar-based vital sign estimation.

BACKGROUND

Applications in the millimeter-wave frequency regime have gained significant interest in the past few years due to the rapid advancement in low cost semiconductor technologies, such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at e.g., 24 GHz, 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal (also referred to as the echo), and determining a distance based on a time delay and/or frequency difference between the transmission and reception of the frequency modulated signal. Accordingly, some radar systems include a transmit antenna to transmit the radio-frequency (RF) signal, and a receive antenna to receive the reflected RF signal, as well as the associated RF circuits used to generate the transmitted signal and to receive the RF signal. In some cases, multiple antennas may be used to implement directional beams using phased array techniques. A multiple-input and multiple-output (MIMO) configuration with multiple chipsets can be used to perform coherent and non-coherent signal processing as well.

SUMMARY

In accordance with an embodiment, a method includes: receiving radar signals with a millimeter-wave radar; generating range data based on the received radar signals; detecting a target based on the range data; performing ellipse fitting on in-phase (I) and quadrature (Q) signals associated with the detected target to generate compensated I and Q signals associated with the detected target; classifying the compensated I and Q signals; when the classification of the compensated I and Q signals correspond to a first class, determining a displacement signal based on the compensated I and Q signals, and determining a vital sign based on the displacement signal; and when the classification of the compensated I and Q signals correspond to a second class, discarding the compensated I and Q signals.

In accordance with an embodiment, a device includes: a millimeter-wave radar configured to transmit chirps and receive reflected chirps; and a processor configured to: generate range data based on the received reflected chirps to generate range data; detect a target based on the range data; perform ellipse fitting on in-phase (I) and quadrature (Q) signals associated with the detected target to generate compensated I and Q signals associated with the detected target; classify the compensated I and Q signals; when the classification of the compensated I and Q signals correspond to a first class, determine a displacement signal based on the compensated I and Q signals, and determine a vital sign based on the displacement signal; and when the classification of the compensated I and Q signals correspond to a second class, discard the compensated I and Q signals.

In accordance with an embodiment, a method of generating a time-domain displacement signal using a millimeter-wave radar includes: receiving reflected chirps with a receiver circuit of the millimeter-wave radar; performing a range FFT on the received reflected chirps to generate range data; detecting a target based on the range data; detecting movement of the detected target by calculating a standard deviation of the range data at a range of the detected target; when the standard deviation is below a first threshold, generating compensated in-phase (I) and quadrature (Q) signals associated with the detected target by performing ellipse fitting on I and Q signals associated with the detected target; classifying the compensated I and Q signals; when the classification of the compensated I and Q signals correspond to a first class, determining the time-domain displacement signal based on the compensated I and Q signals; and when the classification of the compensated I and Q signals correspond to a second class, discarding the compensated I and Q signals.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in a specific context, a radar-based system and method for estimating vital signs (such as respiration rate and heartbeat rate) in a human target. Embodiments of the present invention may be used in non-human targets (such as animals), as wells as for other types of vital signs, such as heart signal shape monitoring, for example.

Embodiments of the present invention may be used in a variety of applications. For example, some embodiments may be used in patient monitoring in hospitals, sleep apnea detection. Some embodiments allow for continuous monitoring of vital signs, which may advantageously lead to better diagnosis by early detection and prevention of critical states of health.

Some embodiments may be used in applications such as presence sensing in homes and offices, driver monitoring in cars, and physiological monitoring in surveillance and earthquake rescue operations. Monitoring the vital signs of, e.g., human targets, finds wide usage in the fields of, e.g., consumer electronics, medical care, surveillance, driver assistance, and industrial applications. Some embodiments may be used in other applications.

In an embodiment of the present invention, a millimeter-wave radar is used to generate a time-domain displacement signal based on in-phase (I) and quadrature (Q) signals associated with a human target, where the time-domain displacement signal is used, e.g., to estimate a vital sign (e.g., heartbeat rate or respiration rate). Random body movements (RBM) and/or intermodulation product (IMP) that may affect the I-Q signals are compensated before the generation of the time-domain displacement signal. The compensated I-Q signals are classified, e.g., as high quality (e.g., data without RBM or IMP) or low quality (e.g., data with RBM or IMP). Low quality data are discarded and not used for estimating the vital sign. In some embodiments, a neural network is used to classify the compensated I-Q signals.

A radar, such as a millimeter-wave radar, may be used to detect and track humans. Once the human targets are identified, the radar may be used to monitor vital signs such as the heartbeat rate and/or respiration rate of the identified human target. In some embodiments, therefore, a radar, such as a millimeter-wave radar, enables a contactless, non-invasive method for vital sensing, which may advantageously increase the comfort of the human target during the vital signs monitoring.

Conventionally, radar-based vital sensing utilizes the discrete Fourier transform and determines respiration rate and heartbeat rate by detecting the maximum peaks in the frequency spectrum. Such an approach may be susceptible to multiple reflections, multipath effects, motion artifacts, RBM and IMP, for example. For example, IMP at a frequency of $f_h$, $f_r$ may occur between the heartbeat rate (e.g., at a frequency $f_h$ between 0.7 Hz and 3 Hz) and a respiration rate (e.g., at a frequency $f_r$ between 0.2 Hz and 0.5 Hz).

Figure 1:
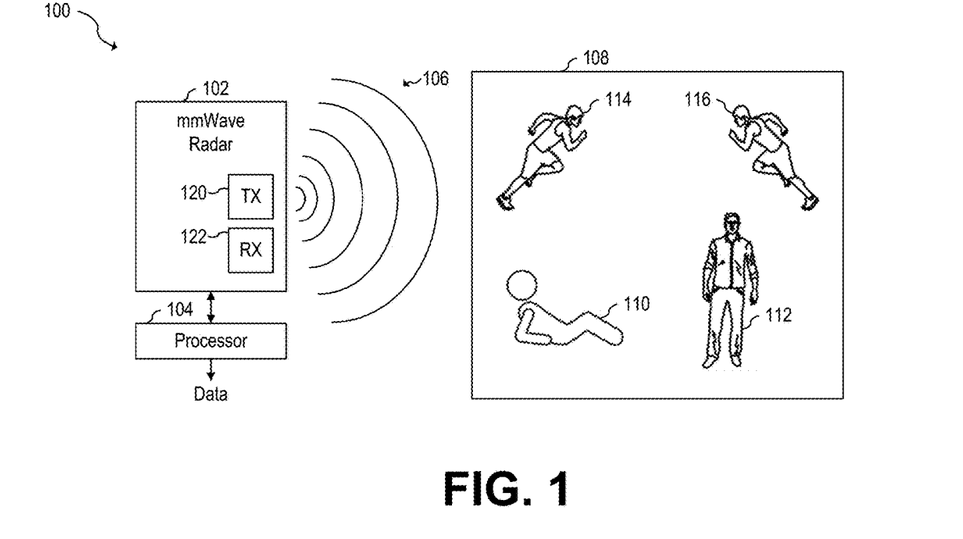
FIG. 1 shows a radar system, according to an embodiment of the present invention.

FIG. 1 shows radar system 100, according to an embodiment of the present invention. Radar system 100 includes millimeter-wave radar 102 and processor 104. In some embodiments, millimeter-wave radar 102 includes processor 104.

During normal operation, millimeter-wave radar 102 transmits a plurality of radiation pulses 106, such as chirps, towards scene 108 using transmitter (TX) circuit 120. In some embodiments the chirps are linear chirps (i.e., the instantaneous frequency of the chirp varies linearly with time).

The transmitted radiation pulses 106 are reflected by objects in scene 108. The reflected radiation pulses (not shown in FIG. 1), which are also referred to as the echo signal, are received by millimeter-wave radar 102 using receiver (RX) circuit 122 and processed by processor 104 to, for example, detect and track targets such as humans.

The objects in scene 108 may include static humans, such as lying human 110, humans exhibiting low and infrequent motions, such as standing human 112, and moving humans, such as running or walking humans 114 and 116. The objects in scene 108 may also include static objects (not shown), such as furniture, and periodic movement equipment. Other objects may also be present in scene 108.

Processor 104 analyses the echo data to determine the location of humans using signal processing techniques. For example, in some embodiments, a range discrete Fourier transform (DFT), such as a range fast Fourier transform (FFT), is used for estimating the range component of the location of a detected human (e.g., with respect to the location of the millimeter-wave radar). The azimuth component of the location of the detected human may be determined using angle estimation techniques.

Processor 104 may be implemented as a general purpose processor, controller or digital signal processor (DSP) that includes, for example, combinatorial circuits coupled to a memory. In some embodiments, processor 104 may be implemented with an ARM architecture, for example. In some embodiments, processor 104 may be implemented as a custom application specific integrated circuit (ASIC). Some embodiments may be implemented as a combination of hardware accelerator and software running on a DSP or general purpose micro-controller. Other implementations are also possible.

Millimeter-wave radar 102 operates as a frequency-modulated continuous-wave (FMCW) radar that includes a millimeter-wave radar sensor circuit, and one or more antenna(s). Millimeter-wave radar 102 transmits (using TX 120) and receives (using RX 122) signals in the 20 GHz to 122 GHz range via the one or more antenna(s) (not shown). Some embodiments may use frequencies outside of this range, such as frequencies between 1 GHz and 20 GHz, or frequencies between 122 GHz, and 300 GHz.

In some embodiments, the echo signals received by millimeter-wave radar 102 are filtered and amplified using band-pass filter (BPFs), low-pass filter (LPFs), mixers, low-noise amplifier (LNAs), and intermediate frequency (IF) amplifiers in ways known in the art. The echo signals are then digitized using one or more analog-to-digital converters (ADCs) for further processing. Other implementations are also possible.

Generally, monitoring a vital signs, such as heartbeat rate or respiration rate of a human target with a radar-based system is a complex endeavor. For example, the amplitude of the heartbeat signal is generally smaller than the amplitude of the respiration signal of the human target. The amplitude of the heartbeat signal is also generally smaller than the amplitude caused by the movement of the human target (e.g., when walking), as well as random body movements of the human target (e.g., such as lifting an arm, twisting the torso, etc.). Additionally, the signal shape of a single heartbeat may be dependent on the subject, the chosen measurement spot, and the distance to the antenna.

In an embodiment of the present invention, compensated I-Q signals are generated using ellipse fitting on the I-Q signals associated with the detected target. A classifier is used to classify the compensated I-Q signals, e.g., as high quality (e.g., without RBM and IMP) or low quality (e.g., with RBM or IMP). I-Q signals classified as low quality are discarded. I-Q signals classified as high quality (e.g., High Quality Data) are used to generate a time-domain displacement signal. The time-domain displacement signal is then filtered and the filtered time-domain displacement signal is used to estimate the vital sign (e.g., the heartbeat rate or respiration rate). In some embodiments, a Kalman filter is used to keep track of the estimated vital sign over time, e.g., as described in co-pending U.S. patent application Ser. No. 16/794,904, filed Feb. 19, 2020, entitled "Radar Vital Signal Tracking Using a Kalman Filter," and incorporated herein by reference. In such embodiments, discarded I-Q signals are not used to update the Kalman filter.

In some embodiments, discarding data inflicted by RBM or IMP advantageously allows for preventing jumps in the estimated vital sign, such as in the estimated heartbeat rate or respiration rate.

Figure 2:
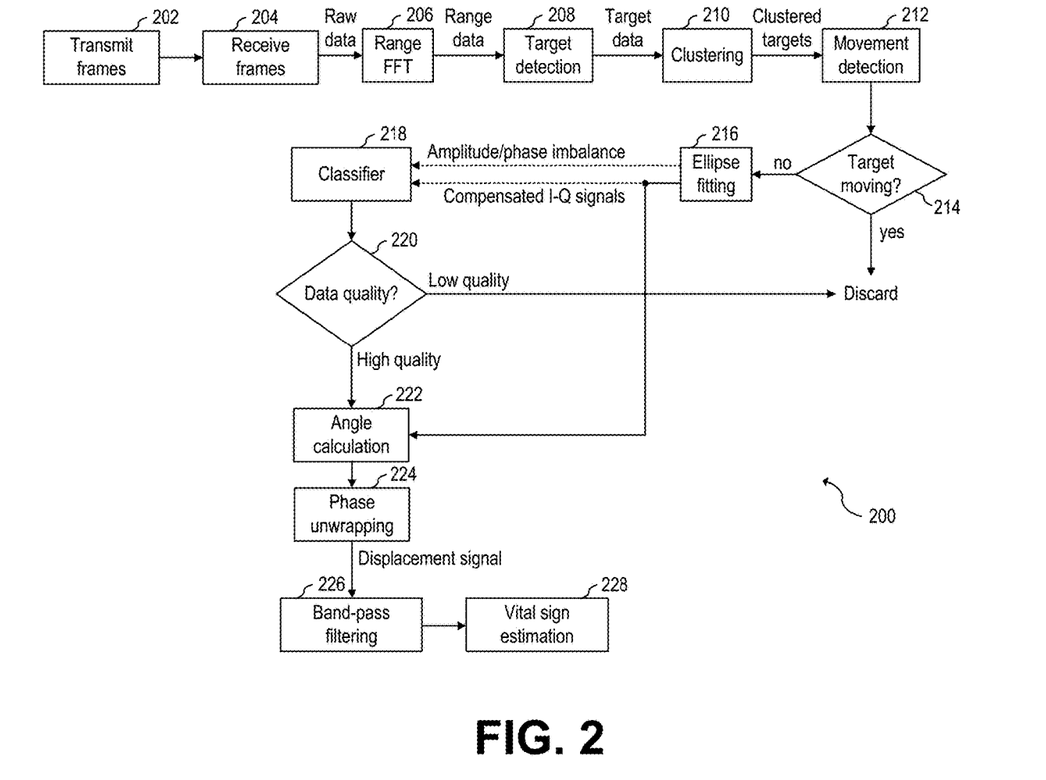
FIG. 2 shows a flow chart of an embodiment method for generating a time-domain displacement signal from reflected radar signals, according to an embodiment of the present invention.

FIG. 2 shows a flow chart of embodiment method 200 for generating a displacement signal from reflected radar signals, according to an embodiment of the present invention. Method 200 may be performed, e.g., by processor 104.

During step 202, millimeter-wave radar 102 transmits, e.g., linear chirps organized in frames using transmitter (TX) circuit 120. The time between chirps of a frame is generally referred to as pulse repetition time (PRT). In some embodiments, the time interval between the end of the last chirp of a frame and the start of the first chirp of the next frame is the same as the PRT so that all chirps are transmitted (and received) equidistantly.

In some embodiments, the chirps have a bandwidth of 2 GHz within the 60 GHz UWB band, the frame time has a duration of 1.28 s, and the PRT is 5 ms (corresponding to an effective sampling rate of 200 Hz).

After reflection from objects, receiver (RX) circuit 122 receives reflected chirps during step 204. During step 204, raw data are generated based on the reflected chirps received by millimeter-wave radar 102. For example, in some embodiments, during step 204, the transmitted and received radar signals are mixed to generate an IF signal. The IF signal may be referred to as the beat signal. The IF signal is then filtered (e.g., with a low-pass and/or band-pass filter) and digitized with an ADC to generate the raw data.

During step 206, a range FFT is performed on the raw data to generate range data. For example, in some embodiments, the raw data are zero-padded and the fast Fourier transform (FFT) is applied to generate the range data, which includes range information of all targets. In some embodiments, the maximum unambiguousness range for the range FFT is based on the PRT, the number of samples per chirp, chirp time, and sampling rate of the analog-to-digital converter (ADC). In some embodiments, the ADC has 12 bits. ADC's with different resolution, such as 10 bits, 14 bits, or 16 bits, for example, can also be used.

In some embodiments, the range FFT is applied on all samples of the observation window. The observation window may be implemented as consecutive windows or as sliding windows and may have a length of one or more frames. For example, in some embodiments, the observation window is implemented as a sliding window in which the length of the observation window corresponds to a plurality of time steps that are evaluated during each time step. For example, in an embodiment in which the time step is equal to 1 frame, and the observation window is a sliding window with 8 frames, then, for each frame, the last 8 frames are used as the observation window. In an embodiment, an observation window with a duration of 8 frames has a duration of about 10 s.

In some embodiments, range data, such as a range image, such as a range-Doppler image or a range cross-range image is generated during step 206.

During step 208, detection of potential targets is performed. For example, in some embodiments, an order statistics (OS) constant false alarm rate (CFAR) (OS-CFAR) detector is performed during step 208. The CFAR detector generates target detection data (also referred to as target data) in which, e.g., "ones" represent targets and "zeros" represent non-targets based, e.g., on the power levels of the range data. For example, in some embodiments, the CFAR detector performs a peak search by comparing the power levels of the range image with a threshold. Points above the threshold are labeled as targets while points below the threshold are labeled as non-targets. Although targets may be indicated by ones and non-targets may be indicated by zeros, it is understood that other values may be used to indicate targets and non-targets.

In some embodiments, targets present in the target data are clustered during step 210 to generate clustered targets (since, e.g., a human target may occupy more than one range bin). Clustering is used to "fuse" the target point cloud belonging to one target to a single target and thus determining the mean range of such single target. For example, in an embodiment, a density-based spatial clustering of applications with noise (DBSCAN) algorithm is used to associate targets to clusters during step 210. The output of DBSCAN is a grouping of the detected points into particular targets. DBSCAN is a popular unsupervised algorithm, which uses minimum points and minimum distance criteria to cluster targets, and may be implemented in any way known in the art. Other clustering algorithms may also be used. The clustered targets are used to identify the range of interest associated with the detected target (the target distance).

During step 212, movement detection of the clustered targets is performed. For example, in some embodiments, calculating the standard deviation on the complex range data at the target distance serves as movement detection. For example, in some embodiments, the complex FFT output is stored in a sliding window. Then, the amplitude of each range bin is summed up along the complete sliding window. The peak in the complete sliding window within chosen minimum and maximum ranges is the target range bin for the current frame, which serves as target detection (step 208). The standard deviation of the range bin of the detected target is indicative of the amount of movement of the target detected at the target range bin.

In some embodiments, data are discarded if the standard deviation in the target range bin along the sliding window is above a first predetermined threshold (movement detection). For example, in some embodiments, if it determined during step 214 that the human target is moving (if the standard deviation in the target range bin along the sliding window is above the first predetermined threshold), data from the current frame may be discarded. It is understood that when it is determined during step 214 that the target is not moving (when the standard deviation is below the first predetermined threshold), the target may be exhibiting some movement, such as movements of the target's hands outside the field of view of the radar, or any other movement that results in a standard deviation below the first predetermined threshold. Such may be the case, for example, of a human target that is sitting or standing, for example.

In some embodiments, data are also discarded during step 214 if the standard deviation in the target range bin along the sliding window is below a second predetermined threshold (to discard static objects such as a chair, for example).

In some embodiments, data are further processed only if, during step 214, the standard deviation in the target range bin along the sliding window is determined to be higher than a low standard deviation threshold and lower than a high standard deviation threshold.

Data not discarded during step 214 is further processed during step 216. During step 216, an ellipse fitting algorithm (also referred to as ellipse correction algorithm) is applied to the I-Q trace (of the complex range data) associated with the detected target to compensate for offset, amplitude, and gain errors. In some embodiments, the compensated data (the compensated I-Q signals) are I-Q signals that correspond to the best fit ellipse associated with the uncompensated I-Q signals. Some embodiments may avoid using the ellipse fitting algorithm, and, e.g., may use an offset compensation algorithm.

The compensated data (the compensated I-Q signals) are provided to a classifier during step 218. During step 218, the classifier estimates the quality of the compensated data and classifies the compensated data as "high quality" (first class) or "low quality" (second class). Low quality compensated data are discarded during step 220, while high quality data are further processed, e.g., in step 222. Exemplary I-Q plots of low quality (low quality data) and high quality (high quality data) are shown in FIGS. 3 and 4, respectively.

Figure 3:
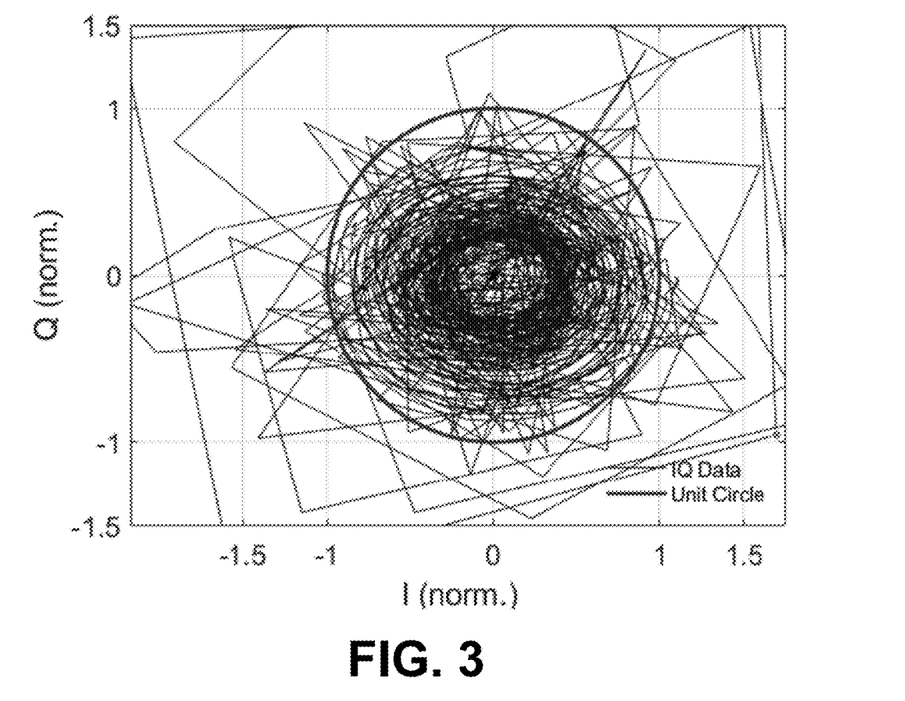
FIGS. 3 and 4 show exemplary in-phase (I) and quadrature (Q) plots of low quality and high quality, respectively.
Figure 4:
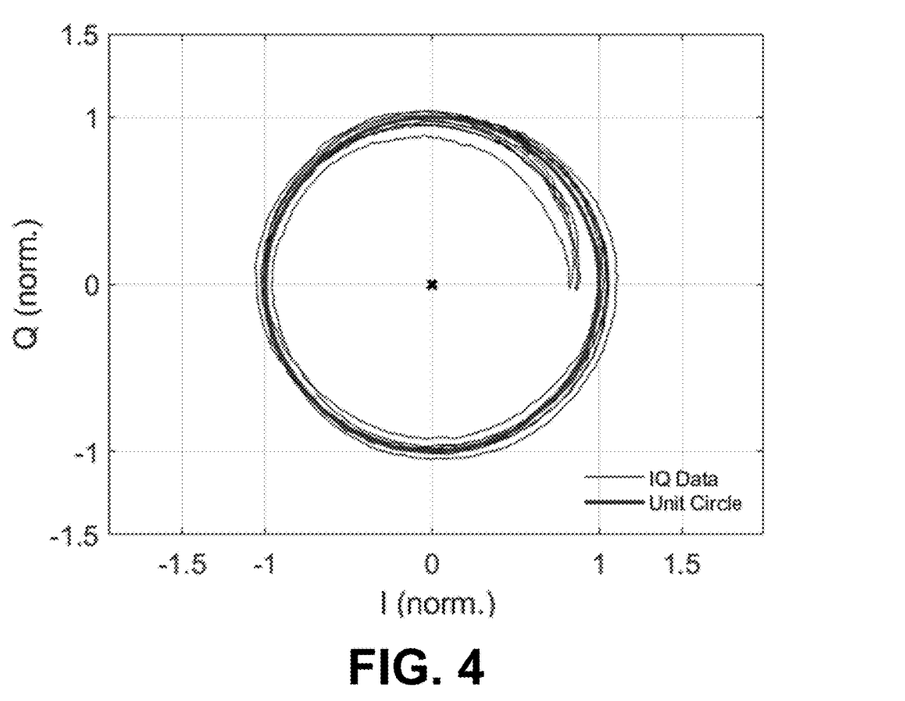

In some embodiments, RBM and IMP associated with the target results in low quality data (e.g., as shown in FIG. 3).

In some embodiments, the classifier used during step 218 is a deep learning-based classified that estimates the quality of the compensated data, e.g., using a neural network. In other embodiments, the quality of the compensated data is estimated based on, e.g., amplitude and phase imbalance values that may be generated during step 216. In other embodiments, the classifier used during step 218 is implemented using a conventional machine learning approach, such as using support-vector machines (SVM), random forest, etc.

During step 222, the angle of the compensated target data is calculated by arctangent demodulation of the I-Q signals from the selected range bin selected during step 208 (the I-Q signals associated with the detected target). The resulting phase values in the range of $[-\pi, +\pi]$ re unwrapped between two consecutive data points during step 224. For example, during step 224, the phase is unwrapped by adding or subtracting $2\pi$ for phase jumps larger than $-\pi$ or $-\pi$, respectively.

In some embodiments, steps 222 and 224 may be performed by calculating the displacement signal as $$D = \frac{\lambda}{4\pi} \cdot \text{unwrap}\left(\arctan\frac{Q}{I}\right) \quad (1)$$

where D represents the time-domain displacement signal, $\lambda$ is the wavelength of the carrier frequency, $\lambda/2$ represents the unambiguousness (phase) range, and I and Q are the in-phase and quadrature-phase components of the carrier, respectively, associated with the detected target.

During step 226, the displacement signal is filtered, and the vital sign estimation is performed during step 228. For example, in some embodiments, a band-pass FIR filter with a pass-band frequency from 0.7 Hz to 3 Hz is used, and a heartbeat frequency estimation is performed during step 228. In some embodiments, a band-pass FIR filter with a pass-band frequency from 0.2 Hz to 0.5 Hz is used, and a respiration frequency estimation is performed during step 228. In some embodiments, a fourth order Butterworth bandpass digital filter with a pass-band from 0.75 Hz to 3.33 Hz is applied to the displacement signal, e.g., for purposes of heartbeat rate estimation. In some embodiments, a fourth order Butterworth bandpass digital filter with a pass-band from 0.2 Hz to 0.33 Hz is applied to the displacement signal, e.g., for purposes of respiration rate estimation. A filter of different order and/or different type, and/or different frequencies may also be applied. In some embodiments, the pass-band of the band-pass filter is adaptive, e.g., as described in co-pending U.S. patent application Ser. No. 16/794,904, filed Feb. 19, 2020, entitled "Radar Vital Signal Tracking Using a Kalman Filter," and incorporated herein by reference.

In some embodiments, a plurality of bandpass filters are, e.g., simultaneously applied to the time-domain displacement signal to estimate a corresponding plurality of vital signs. For example, some embodiments include a first band-pass filter for heartbeat rate estimation and a second band-pass filter for respiration rate estimation.

Figure 5:
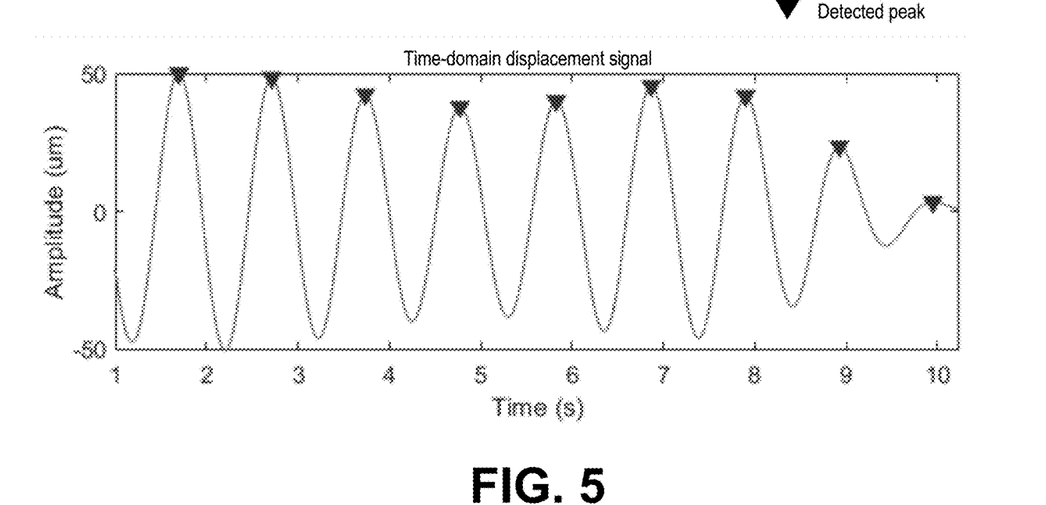
FIG. 5 shows a filtered time-domain displacement signal of a heartbeat of a human target, according to an embodiment of the present invention.

In some embodiments, the vital sign estimation is performed during step 228 by counting the number of peaks that the filtered time-domain displacement signal exhibits in a period of time, or by measuring a time between detected peaks of the filtered time-domain displacement signal. For example, FIG. 5 shows a filtered time-domain displacement signal of the heartbeat of a human target, according to an embodiment of the present invention. In the example of FIG. 5, the heartbeat rate is determined by counting the number of peaks in a period of time, which in this case results in a heartbeat rate estimation of 58 bpm.

Figure 6:
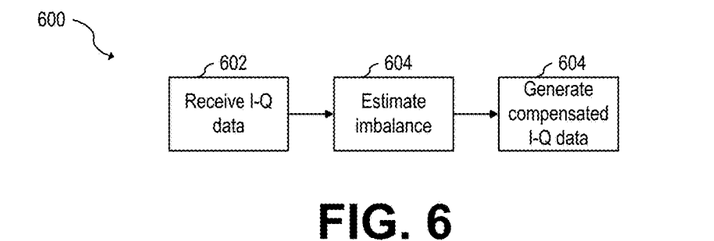
FIG. 6 shows a flow chart of an embodiment method for performing the ellipse fitting step of FIG. 2, according to an embodiment of the present invention.

FIG. 6 shows a flow chart of embodiment method 600 for performing ellipse fitting step 216, according to an embodiment of the present invention.

During step 602, the I-Q data corresponding to the clustered target are received (e.g., from step 214). The I and Q signals may be represented as $$I = A_I \cos\left(\frac{4\pi d(t)}{\lambda} + \phi_I\right) + B_I \quad (2)$$

$$Q = A_Q \sin\left(\frac{4\pi d(t)}{\lambda} + \phi_Q\right) + B_Q \quad (3)$$

where d(t) is the time-varying displacement signal, $B_I$ and $B_Q$ represent DC offsets, $\lambda$ is the wavelength of the carrier frequency.

During step 604, the amplitude and phase imbalance are estimated. For example, The amplitude imbalance $A_e$ and the phase imbalance $\phi_e$ may be given by $$A_e = \frac{A_Q}{A_I} \quad (4)$$

$$\phi_e = \phi_Q - \phi_I \quad (5)$$

As shown, for example, in A. Singh et al., "Data-Based Quadrature Imbalance Compensation for a CW Doppler Radar System," published in IEEE Transactions on Microwave Theory and Techniques, vol. 61, no. 4, pp. 1718-1724, April 2013, the amplitude imbalance $A_e$ and the phase imbalance $\phi_e$ may be calculated by $$A_e = \sqrt{\frac{1}{A}} \quad (6)$$

$$\phi_e = \sin^{-1}\left(\frac{B}{2\sqrt{A}}\right) \quad (7)$$

where the normalized equation of an ellipse (where I is represented in the horizontal axis and Q is represented in the vertical axis) may be given as $$I^2 + A \times Q^2 + B \times IQ + C \times I + D \times Q + E = 0 \quad (8)$$

The best solution for A, B, C, D, and E may be found as $$\begin{bmatrix} A \\ B \\ C \\ D \\ E \end{bmatrix} = (M^T M)^{-1} M^T b \quad (9)$$

where M and b are given by $$M = \begin{bmatrix} Q_1^2 & I_1 Q_1 & I_1 & Q_1 & 1 \\ \vdots & \vdots & \vdots & \ddots & \vdots \\ Q_N^2 & I_N Q_N & I_N & \ldots & 1 \end{bmatrix} \quad (10)$$

$$b = \begin{bmatrix} -I_1^2 \\ \vdots \\ -I_N^2 \end{bmatrix} \quad (11)$$

where N is the number of (I,Q) samples.

Once Equation 9 is solved, the amplitude imbalance $A_e$ and the phase imbalance $\phi_e$ may be calculated using Equations 6 and 7.

Once the amplitude imbalance $A_e$ and the phase imbalance $\phi_e$ are determined, the compensated I-Q data are generated, for example, using the Gram Schmidt (GS) or ellipse fitting method in a known manner, during step 604.

Figure 7:
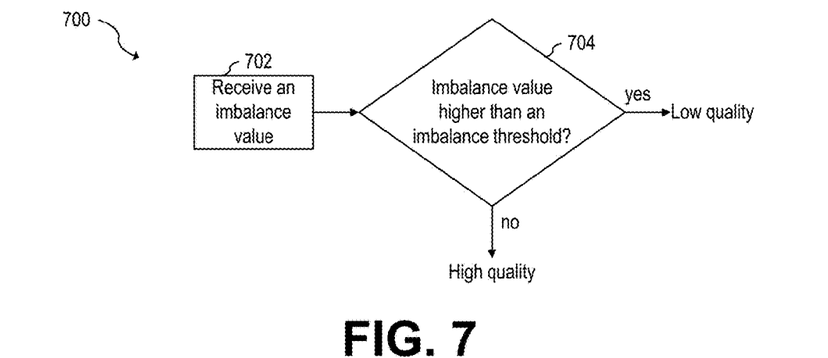
FIGS. 7 and 8 show flow charts of embodiment methods for performing the classification step of FIG. 2, according to embodiments of the present invention.

FIG. 7 shows a flow chart of embodiment method 700 for performing classification steps 218 and 220, according to an embodiment of the present invention.

During step 702, an imbalance value is received (e.g., determined during step 604). In some embodiments, the imbalance value may be, e.g., the amplitude imbalance $A_e$ or the phase imbalance $\phi_e$ calculated during step 604.

During step 704, the imbalance value is compared with an imbalance threshold. If the imbalance value is higher than the imbalance threshold, the compensated I-Q-data (e.g., generated during step 604) is classified as low quality. If the imbalance value is lower than the imbalance threshold, the compensated I-Q data are classified as high quality.

In some embodiments, if either of the amplitude imbalance $A_e$ or the phase imbalance $\phi_e$ is higher than a respective threshold, the compensated I-Q data are classified as low quality.

Figure 8:
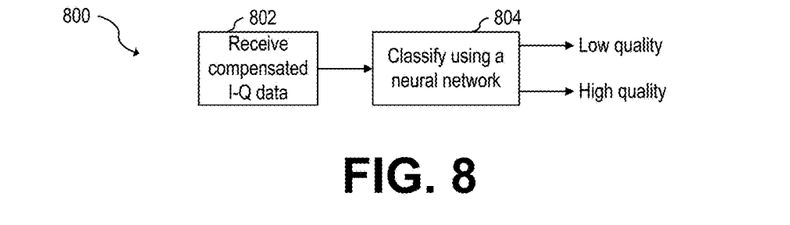

FIG. 8 shows a flow chart of embodiment method 800 for performing classification steps 218 and 220, according to an embodiment of the present invention.

During step 802, compensated I-Q data are received (e.g., determined during step 604). During step 804, the compensated I-Q data are fed through a neural network. The neural network classifies the compensated I-Q data as low quality or high quality based on the neural network model.

Figure 9:
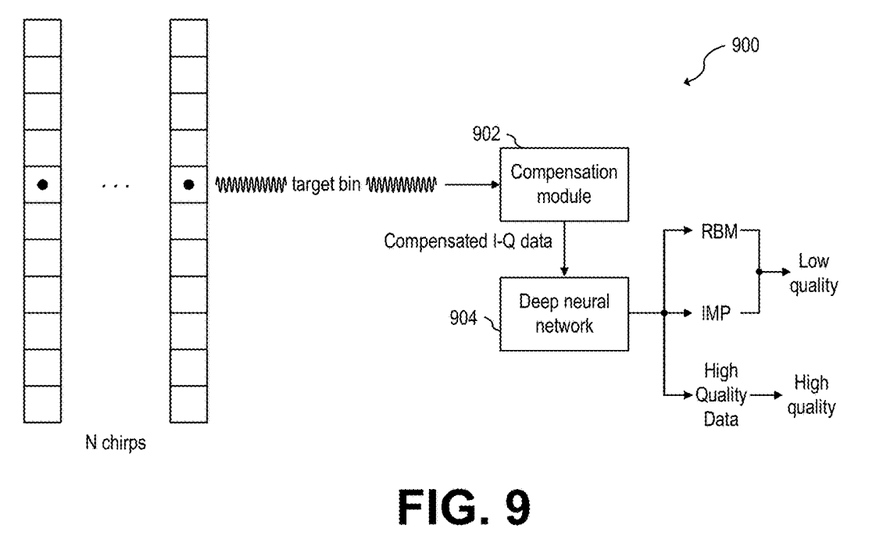
FIG. 9 shows a block diagram of an embodiment for classifying I-Q data using a deep neural network, according to an embodiment of the present invention.

FIG. 9 shows a block diagram of embodiment 900 for classifying I-Q data using deep neural network 904, according to an embodiment of the present invention.

As shown in FIG. 9, after reception of N chirps (e.g., 2048 chirps) from one or more consecutive frames (e.g., 8 consecutive frames), a target bin is identified (e.g., in step 208). Compensation module 902 receives I-Q data associated with the target bin (e.g., in step 602) and produces compensated I-Q data (e.g., in step 604). Deep neural network classifier 904 receives the compensated I-Q data (e.g., in step 802) and perform a multilevel classification. For example, in some embodiments, the compensated I-Q data are divided into 3 classes: RBM, IMP, and High Quality Data. Only I-Q data that is classified as "High Quality Data" is categorized as high quality (e.g., in step 220). I-Q data classified as RBM or IMP is categorized as low quality (e.g., in step 220) and discarded.

In some embodiments, classifier 904 may be implemented with one-dimensional (1D) convolutional neural network (CNN) layers. In some embodiments, the 1D CNN model advantageously learns from the I-Q time series directly.

In some embodiments, a long-short term memory (LSTM) model may be used instead of the 1D CNN model.

Figure 10:
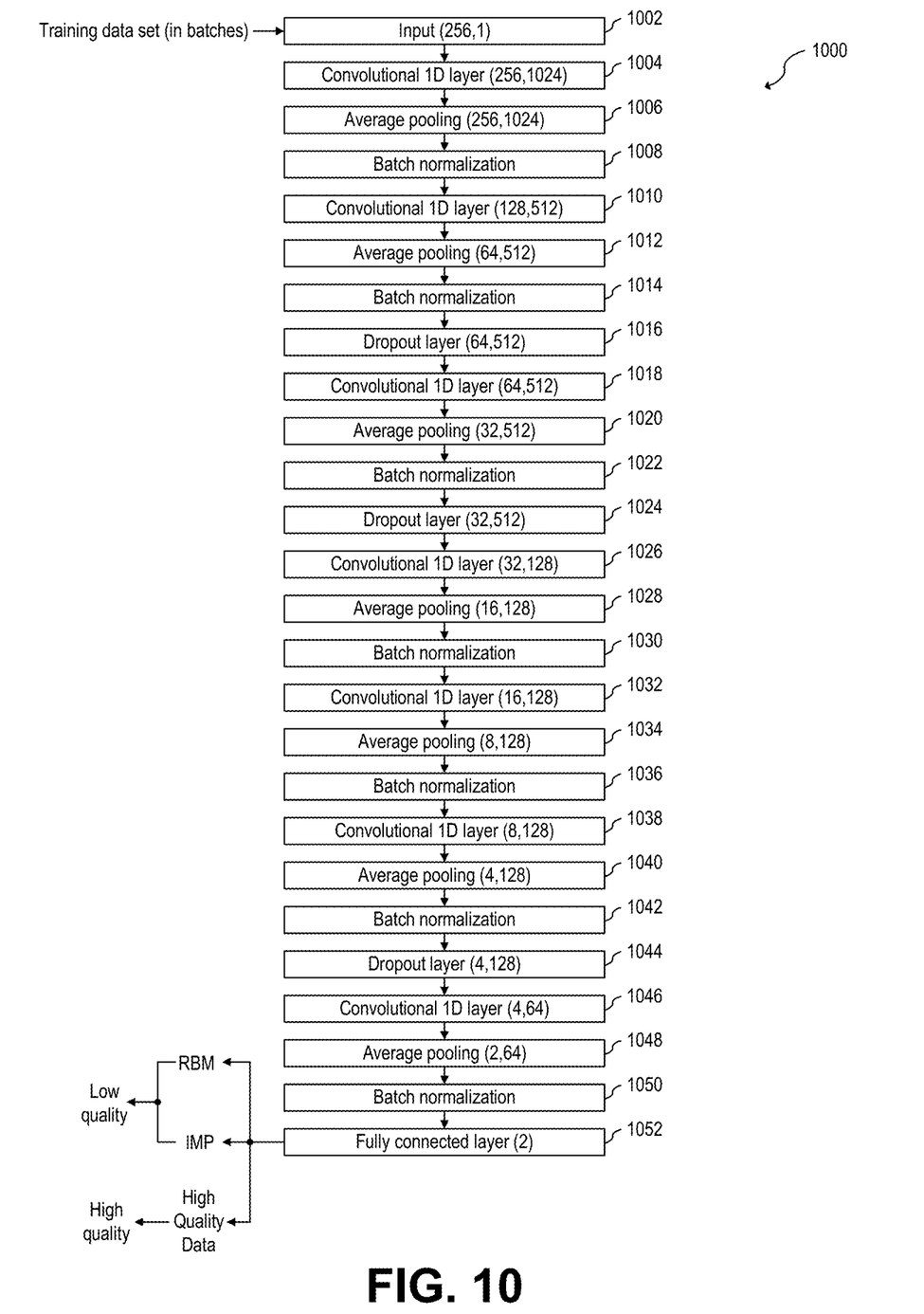
FIGS. 10 and 11 show block diagrams of the training of the deep neural network of FIG. 9, and of the trained deep neural network of FIG. 9, respectively, according to an embodiment of the present invention.

FIG. 10 shows a block diagram of training deep neural network 1000, according to an embodiment of the present invention. Deep neural network 904 may be trained as training deep neural network 1000. Training deep neural network 1000 includes input layer 1002, convolutional 1D layers 1004, 1010, 1018, 1026, 1032, 1038, and 1046, average pooling layers 1006, 1012, 1020, 1028, 1034, 1040, and 1048, batch normalization layers 1008, 1014, 1022, 1030, 1036, 1042, and 1050, dropout layers 1016, 1024, and 1044, and fully connected layer 1052. Different arrangements (e.g., different number of layers and/or different types of layers) may also be used.

As shown in FIG. 10, deep neural network 1000 receives batches (e.g., of 20 samples each) of training data with input layer 1002 and generates, with fully connected layer 1052, an M-element vector that corresponds to the classification of the respective data, where M is equal to or greater than 2. For example, in some embodiments, M is equal to 3, the output vector is in the form of, e.g., ["RBM" "IMP" "High Quality Data"], and the training data includes I-Q data (e.g., I-Q time series) that are pre-labeled as RBM, IMP, or High Quality Data. For example, an output vector [1 0 0] represents an "RBM" classification for the respective data; an output vector [0 1 0] represents an "IMP" classification for the respective data; and an output vector [0 0 1] represents a "High Quality Data" classification for the respective data.

In some embodiments, the output vector includes confidence values (i.e., the probability that a particular label is correct. In such embodiments, an output vector [0.8 0.15 0.05] may be interpreted as the respective data having 80% probability of corresponding to an "RBM" classification, a 15% probability of corresponding to an "IMP" classification, and a 5% probability of corresponding to a "High Quality Data" classification. In such scenario, the respective data may be assigned the classification with highest confidence (in this non-limiting example, classified as "RBM").

In some embodiments, training data are pre-labeled as RBM when the amplitude imbalance $A_e$ or the phase imbalance $\phi_e$ is higher than a respective threshold. In some embodiments, training data are pre-labeled as IMP when the difference between estimated and reference heartbeat rate is similar to the corresponding respiration rate of the human target. In some embodiments, training data are pre-labeled as High Quality Data when the criteria for RBM and IMP are not met. In some embodiments, the training data may be pre-labeled in a different manner.

During normal operation, input layer 1002 receives the training data in the form of, e.g., a 256×1 one-dimensional signals (256 data points in slow time).

The convolutional 1D layers (1004, 1010, 1018, 1026, 1032, 1038, and 1046) convolve their respective inputs and pass its results to the next layer. For example, as shown in FIG. 10, convolutional 1D layers 1004 convolves 256 slow-time data using 1024 filters; convolutional 1D layers 1010 convolves 128 slow-time data using 512 filters; convolutional 1D layers 1018 convolves 64 slow-time data using 512 filters; convolutional 1D layers 1026 convolves 32 slow-time data using 128 filters; convolutional 1D layers 1032 convolves 16 slow-time data using 128 filters; convolutional 1D layers 1038 convolves 8 slow-time data using 128 filters; and convolutional 1D layers 1046 convolves 4 slow-time data using 64 filters. Other implementations are also possible.

In some embodiments, the type of convolution filters used in the convolutional 1D layers (1004, 1010, 1018, 1026, 1032, 1038, and 1046) has a size of 3×3. Some embodiments may use other filter sizes.

Each convolutional 1D layer (1004, 1010, 1018, 1026, 1032, 1038, and 1046) uses a rectified linear unit (ReLU) as activation function. Other activation functions may also be used.

The pooling layers (1006, 1012, 1020, 1028, 1034, 1040, and 1048) smoothen the data by, e.g., applying averaging. For example, as shown in FIG. 10, pooling layer 1006 filters 256 slow-time data using 1024 filters; pooling layer 1012 filters 64 slow-time data using 512 filters; pooling layer 1020 filters 32 slow-time data using 512 filters; pooling layer 1028 filters 16 slow-time data using 128 filters; pooling layer 1034 filters 8 slow-time data using 128 filters; pooling layer 1040 filters 4 slow-time data using 128 filters; and pooling layer 1048 filters 2 slow-time data using 64 filters. Other implementations are also possible.

In some embodiments, each pooling layer has a size of 2×2 with strides 2 (the filter window is shifted by 2 units to the right and down for application of the next pooling in the neighborhood). Some embodiments may use other filter sizes and a different stride.

As shown in FIG. 10, each pooling layer (1006, 1012, 1020, 1028, 1034, 1040, and 1048) applies average pooling (using an average function). In some embodiments, a "max" function may also be used.

Batch normalization layers (1008, 1014, 1022, 1030, 1036, 1042, and 1050), subtracts the mean of the respective batch data being processed from the batch data, and the result is divided by the standard deviation of the batch data so that the batch data is normalized (so that the resulting mean is 0 and the resulting standard deviation is 1).

Dropout layers (1016, 1024, and 1044) help create redundancy in the neural network by randomly removing nodes (e.g., randomly zeroing weights on the previous convolutional layer) and corresponding edges to/from the removed nodes of the neural network. In some embodiments, 20% of the nodes are removed by each of the dropout layers. In the embodiment shown in FIG. 10, dropout layer 1016 has a spatial domain with 64 dimensions and 512 filters; dropout layer 1024 has a spatial domain with 32 dimensions and 512 filters; and dropout layer 1044 has a spatial domain with 4 dimensions and 128 filters. Other implementations are also possible.

Fully connected layer 1052 that uses, e.g., a softmax as an activation function is used to generate an M-element vector corresponding to the classification of the batch data.

During training, the generated output vector is compared with the pre-labels of the respective data batch, and the weights of the neural network are adjusted so that the classification of a respective batch of data corresponds to the respective pre-labels. The model (the neural network 1000) is refined by running a plurality of training data batches, e.g., thousands of training data batches. In some embodiments, an adaptive moment estimation (Adam) is used to optimize the deep neural network 1000.

Figure 11:
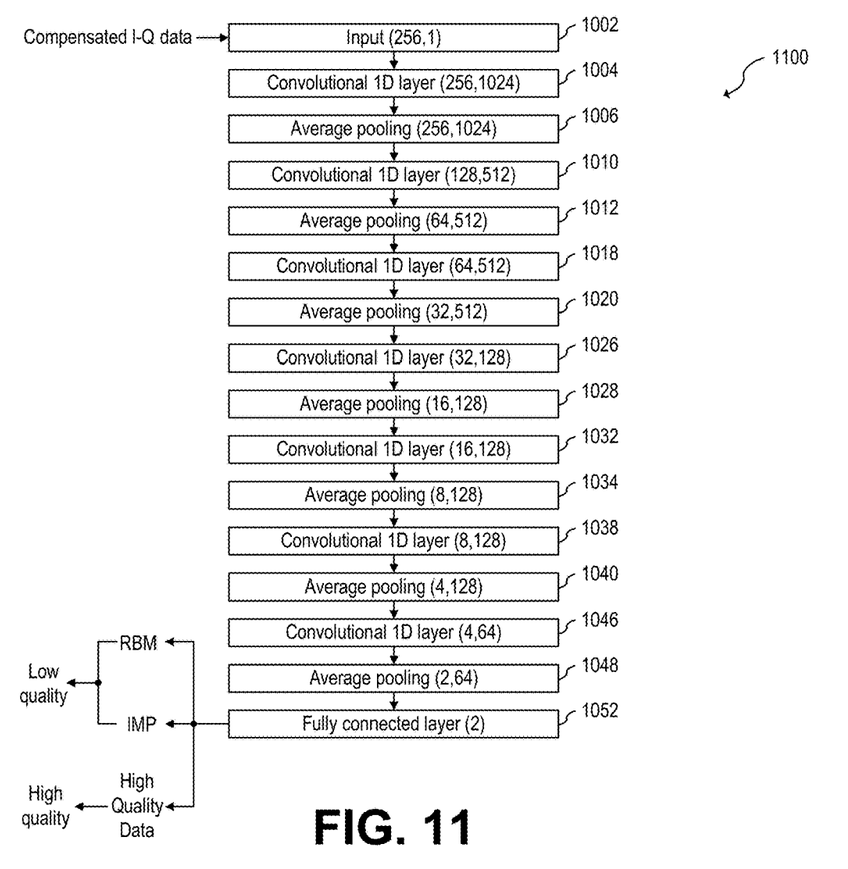

Once trained, the trained deep neural network may be used during steps 218 and 220 to classify the compensated I-Q data. FIG. 11 shows trained deep neural network 1100, according to an embodiment of the present invention. Deep neural network 1100 may have been trained, e.g., as described in with respect to FIG. 10. Deep neural network 904 may be implemented as deep neural network 1100.

In some embodiments, a difference between the training model (e.g., training deep neural network 1000 of FIG. 10) and the inference model (e.g., trained deep neural network 1100 of FIG. 11) is the batch normalization. For example, in the training model, the batch normalization (1008, 1014, 1022, 1030, 1036, 1042, and 1050) is computed across the mini-batch used for training the network (i.e. mean and variance across the batch is computed). In the inference model, the learned global mean and variance is used (not learned) for normalization (normalization is not shown in FIG. 11).

During normal operation, input layer 1002 receives compensated I-Q data (e.g., generated during step 216). The training convolutional 1D layers and pooling layers process the received I-Q data, and fully connected layer generates a, e.g., 3-element vector that classifies the received I-Q data as, e.g., RBM, IMP, or High Quality Data. I-Q data classified as RBM or IMP is categorized as low quality (in step 220) and discarded. I-Q data classified as High Quality Data are further processed in steps 222, 224, 226, and 228.

Advantages of some embodiments include that by avoiding estimating the vital sign when the quality of the I-Q signal is low (e.g., due to RBM or IMP), jumps in the estimated vital sign (e.g., jumps in the heartbeat rate or respiration rate) may be prevented.

In some embodiments, estimating the vital sign based on a time-domain radar-based displacement advantageously allows for removal of IMP and RBM when compared with vital sign estimation methods that rely on spectral analysis and that are susceptible to corrupted estimates due to RBM and IMP, given the sensitivities of the phase in the IF signal due to minute displacements of the human target.

Example embodiments of the present invention are summarized here. Other embodiments can also be understood from the entirety of the specification and the claims filed herein.

Example 1. A method including: receiving radar signals with a millimeter-wave radar; generating range data based on the received radar signals; detecting a target based on the range data; performing ellipse fitting on in-phase (I) and quadrature (Q) signals associated with the detected target to generate compensated I and Q signals associated with the detected target; classifying the compensated I and Q signals; when the classification of the compensated I and Q signals correspond to a first class, determining a displacement signal based on the compensated I and Q signals, and determining a vital sign based on the displacement signal; and when the classification of the compensated I and Q signals correspond to a second class, discarding the compensated I and Q signals.

Example 2. The method of example 1, where classifying the compensated I and Q signals includes using a neural network.

Example 3. The method of one of examples 1 or 2, where the neural network includes a one-dimensional (1D) convolutional neural network (CNN) layer.

Example 4. The method of one of examples 1 to 3, where the neural network includes a fully-connected layer.

Example 5. The method of one of examples 1 to 4, further including training the neural network.

Example 6. The method of one of examples 1 to 5, further including: generating an amplitude imbalance value and a phase imbalance value associated with the compensated I and Q signals of the detected target; and classifying the compensated I and Q signals as the first class when the amplitude imbalance value is lower than a first threshold, and when the phase imbalance value is lower than a second threshold.

Example 7. The method of one of examples 1 to 6, further including: generating an amplitude imbalance value and a phase imbalance value associated with the compensated I and Q signals of the detected target; and classifying the compensated I and Q signals as the second class when the amplitude imbalance value is higher than a first threshold, or when the phase imbalance value is higher than a second threshold.

Example 8. The method of one of examples 1 to 7, where determining the displacement signal includes determining an angle of arrival based on the compensated I and Q signals.

Example 9. The method of one of examples 1 to 8, where determining the vital sign includes filtering the displacement signal, and estimating heartbeat rate or respiration rate based on the filtered displacement signal.

Example 10. The method of one of examples 1 to 9, where determining the vital sign includes using a Kalman filter to track changes of the vital sign over time.

Example 11. The method of one of examples 1 to 10, where discarding the compensated I and Q signals includes avoiding updating the Kalman filter with the compensated I and Q signals.

Example 12. The method of one of examples 1 to 11, where detecting the target includes performing a peak search based on the range data.

Example 13. The method of one of examples 1 to 12, where generating the range data includes performing a range FFT on the received radar signals.

Example 14. The method of one of examples 1 to 13, further including transmitting radar signals, where the received radar signals are based on the transmitted radar signals.

Example 15. A device including: a millimeter-wave radar configured to transmit chirps and receive reflected chirps; and a processor configured to: generate range data based on the received reflected chirps to generate range data; detect a target based on the range data; perform ellipse fitting on in-phase (I) and quadrature (Q) signals associated with the detected target to generate compensated I and Q signals associated with the detected target; classify the compensated I and Q signals; when the classification of the compensated I and Q signals correspond to a first class, determine a displacement signal based on the compensated I and Q signals, and determine a vital sign based on the displacement signal; and when the classification of the compensated I and Q signals correspond to a second class, discard the compensated I and Q signals.

Example 16. The device of example 15, where the processor is configured to classify the compensated I and Q signals using a neural network that includes a one-dimensional (1D) convolutional neural network (CNN) layer.

Example 17. The device of one of examples 15 or 16, where the processor is configured to determine the displacement signal as $$D = \frac{\lambda}{4\pi} \cdot \text{unwrap}\left(\arctan\frac{Q}{I}\right),$$

where $\lambda$ is a wavelength of a carrier frequency of the transmitted chirps, and where I and Q are the in-phase and quadrature-phase components, respectively, associated with the detected target.

Example 18. A method of generating a time-domain displacement signal using a millimeter-wave radar, the method including: receiving reflected chirps with a receiver circuit of the millimeter-wave radar; performing a range FFT on the received reflected chirps to generate range data; detecting a target based on the range data; detecting movement of the detected target by calculating a standard deviation of the range data at a range of the detected target; when the standard deviation is below a first threshold, generating compensated in-phase (I) and quadrature (Q) signals associated with the detected target by performing ellipse fitting on I and Q signals associated with the detected target; classifying the compensated I and Q signals; when the classification of the compensated I and Q signals correspond to a first class, determining the time-domain displacement signal based on the compensated I and Q signals; and when the classification of the compensated I and Q signals correspond to a second class, discarding the compensated I and Q signals.

Example 19. The method of example 18, where generating the compensated I and Q signals includes using a Gram Schmidt (GS) or ellipse correction method.

Example 20. The method of one of examples 18 or 19, where classifying the compensated I and Q signals includes using a neural network that includes a one-dimensional (1D) convolutional neural network (CNN) layer.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method comprising:
   transmitting chirps with a millimeter-wave radar;
   receiving reflected chirps with the millimeter-wave radar;
   performing, by a processor, the steps of:
   generating range data based on the received reflected chirps;
   detecting a target based on the range data;
   performing ellipse fitting on in-phase (I) and quadrature (Q) signals associated with the detected target to generate compensated I and Q signals associated with the detected target;
   generating an amplitude imbalance value and a phase imbalance value associated with the compensated I and Q signals of the detected target;
   classifying the compensated I and Q signals as a first class when the amplitude imbalance value is lower than a first threshold and the phase imbalance value is lower than a second threshold;
   classifying the compensated I and Q signals as a second class when the amplitude imbalance value is higher than the first threshold, or when the phase imbalance value is higher than the second threshold;
   when the classification of the compensated I and Q signals correspond to the first class, determining a displacement signal based on the compensated I and Q signals, and determining a vital sign based on the displacement signal; and
   when the classification of the compensated I and Q signals correspond to the second class, discarding the compensated I and Q signals.

2. The method of claim 1, wherein classifying the compensated I and Q signals comprises using a neural network.

3. The method of claim 2, wherein the neural network comprises a one-dimensional (1D) convolutional neural network (CNN) layer.

4. The method of claim 2, wherein the neural network comprises a fully-connected layer.

5. The method of claim 2, further comprising training the neural network.

6. The method of claim 1, wherein determining the displacement signal comprises determining an angle of arrival based on the compensated I and Q signals.

7. The method of claim 1, wherein determining the vital sign comprises filtering the displacement signal, and estimating heartbeat rate or respiration rate based on the filtered displacement signal.

8. The method of claim 1, wherein determining the vital sign comprises using a Kalman filter to track changes of the vital sign over time.

9. The method of claim 8, wherein discarding the compensated I and Q signals comprises avoiding updating the Kalman filter with the compensated I and Q signals.

10. The method of claim 1, wherein detecting the target comprises performing a peak search based on the range data.

11. The method of claim 1, wherein generating the range data comprises performing a range FFT on the received reflected chirps.

12. A device comprising:
   a millimeter-wave radar configured to transmit chirps and receive reflected chirps; and
   a processor configured to:
   generate range data based on the received reflected chirps to generate range data;
   detect a target based on the range data;
   perform ellipse fitting on in-phase (I) and quadrature (Q) signals associated with the detected target to generate compensated I and Q signals associated with the detected target;
   generate an amplitude imbalance value and a phase imbalance value associated with the compensated I and Q signals of the detected target;
   classify the compensated I and Q signals as a first class when the amplitude imbalance value is lower than a first threshold and the phase imbalance value is lower than a second threshold;
   classify the compensated I and Q signals as a second class when the amplitude imbalance value is higher than the first threshold, or when the phase imbalance value is higher than the second threshold;
   when the classification of the compensated I and Q signals correspond to the first class, determine a displacement signal based on the compensated I and Q signals, and determine a vital sign based on the displacement signal; and
   when the classification of the compensated I and Q signals correspond to the second class, discard the compensated I and Q signals.

13. The device of claim 12, wherein the processor is configured to classify the compensated I and Q signals using a neural network that comprises a one-dimensional (1D) convolutional neural network (CNN) layer.

14. The device of claim 12, wherein the processor is configured to determine the displacement signal as $$D = \frac{\lambda}{4\pi} \cdot \text{unwrap}\left(\arctan\frac{Q}{I}\right),$$

wherein $\lambda$ is a wavelength of a carrier frequency of the transmitted chirps, and wherein I and Q are the in-phase and quadrature-phase components, respectively, associated with the detected target.

15. A method of generating a time-domain displacement signal using a millimeter-wave radar, the method comprising:
   transmitting chirps with the millimeter-wave radar;
   receiving reflected chirps with a receiver circuit of the millimeter-wave radar;
   performing, by a processor, the steps of:
   performing a range FFT on the received reflected chirps to generate range data;
   detecting a target based on the range data;
   detecting movement of the detected target by calculating a standard deviation of the range data at a range of the detected target;
   when the standard deviation is below a threshold, generating compensated in-phase (I) and quadrature (Q) signals associated with the detected target by performing ellipse fitting on I and Q signals associated with the detected target;

generating an amplitude imbalance value and a phase imbalance value associated with the compensated I and Q signals of the detected target;

classifying the compensated I and Q signals as a first class when the amplitude imbalance value is lower than a first threshold and the phase imbalance value is lower than a second threshold;

classifying the compensated I and Q signals as a second class when the amplitude imbalance value is higher than the first threshold, or when the phase imbalance value is higher than the second threshold;

when the classification of the compensated I and Q signals correspond to the first class, determining the time-domain displacement signal based on the compensated I and Q signals; and when the classification of the compensated I and Q signals correspond to the second class, discarding the compensated I and Q signals.

16. The method of claim 15, wherein generating the compensated I and Q signals comprises using a Gram Schmidt (GS) or ellipse correction method.

17. The method of claim 15, wherein classifying the compensated I and Q signals comprises using a neural network that comprises a one-dimensional (1D) convolutional neural network (CNN) layer.

* * * * *

UNITED STATES PATENT AND TRADEMARK OFFICE
CERTIFICATE OF CORRECTION

PATENT NO. : 11,585,891 B2
APPLICATION NO. : 16/853011
DATED : February 21, 2023
INVENTOR(S) : Santra Page 1 of 1

It is certified that error appears in the above-identified patent and that said Letters Patent is hereby corrected as shown below:

In the Claims

Claim 1, Column 15, Line 30; insert --when-- between "and" and "the".

Claim 12, Column 16, Line 21; insert --when-- between "and" and "the".

Claim 15, Column 17, Line 6; insert --when-- between "and" and "the".

Signed and Sealed this
Fourth Day of April, 2023

Katherine Kelly Vidal
*Director of the United States Patent and Trademark Office*